US005684242A

United States Patent [19]
Schnable et al.

[11] Patent Number: 5,684,242
[45] Date of Patent: Nov. 4, 1997

[54] NUCLEAR RESTORER GENES FOR HYBRID SEED PRODUCTION

[75] Inventors: Patrick S. Schnable; Roger P. Wise, both of Ames, Iowa

[73] Assignees: Iowa State University Research Foundation, Inc., Ames, Iowa; The United States of America as represented by the Secretary of Agriculture, Washington, D.C.

[21] Appl. No.: 346,611

[22] Filed: Nov. 29, 1994

[51] Int. Cl.$^6$ .................. C12N 15/00; C12N 15/82; A01H 1/06; A01H 11/00
[52] U.S. Cl. .................. 800/205; 435/172.3; 435/69.1; 536/24.3; 536/23.6; 935/9; 47/58
[58] Field of Search .................. 47/58.03, 58.08; 800/200, 205; 435/172.3, 9.1; 536/24.3, 23.6; 935/9

[56] References Cited

U.S. PATENT DOCUMENTS 4,751,347  6/1988  Erickson .................. 47/58

OTHER PUBLICATIONS

Aarts et al., *Nature*, 363, 715–717 (1993).
Albertsen et al., *Can. J. Genet. Cytol.*, 23, 195–208 (1981).
Bailey–Serres et al., *Theor. Appl. Genet.*, 73, 252–260 (1986).
Braun et al., *Plant Cell*, 2, 153–161 (1990).
Dewey et al., *Proc. Nat'l. Acad. Sci. USA*, 84, 5374–5378 (1987).
Dixon et al., *Theor. Appl. Genet.*, 63, 75–80 (1982).
Forde et al., *Proc. Nat'l. Acad. Sci. USA*, 75, 3841–3845 (1978).
Huang et al., *EMBOJ*, 9, 339–247 (1990).
Janska et al., *Genetics*, 135, 869–879 (1993).
Kamps, T., et al., *Maize Genet. Coop. Newsl.*, 66, 45 (1992).
Kennell et al., *Mol. Gen. Genet.*, 210, 399–406 (1987).

Korth et al., *Proc. Nat'l. Acad. Sci. USA*, 88, 10865–10869 (1991).
Laughnan et al., *Ann. Rev. Genet.*, 17, 27–48 (1983).
Laver et al., *The Plant Journal*, 1, 185–193 (1991).
Levings, *Plant Cell*, 5, 1285–1290 (1993).
Levings et al., *Cell*, 56, 171–179 (1989).
Mann et al., *Theor. Appl. Genet.*, 78, 293–297 (1989).
Mariani et al., *Nature*, 347, 737–741 (1990).
Nivison et al., *Plant Cell*, 1, 1121–1130 (1989).
Pring et al., *Genetics*, 89, 121–136 (1978).
Pring et al., *Ann. Rev. Phytopathol.*, 27, 483–502 (1989).
Schardl et al., *Cell*, 43, 361–368 (1985).
Schnable et al., *Genetics*, 136, 1171–1185 (1994).
Singh et al., *Plant Cell*, 3, 1349–1362 (1991).
Sisco, *Crop Sci.*, 31, 1263–1266 (1991).
Wise et al., *Proc. Nat'l. Acad. Sci. USA*, 84, 2858–286 (1987a).
Wise et al., *Plant Mol. Biol.*, 9, 121–126 (1987b).
Wise et al., *Theor. Appl. Genet.*, 88, 785–795 (1994).
Rongnoparut et al. (1991) Isolation and characterization of a cytosolic aldehyde dehydrogenase encoding DNA from mouse liver. Gene vol. 101 pp. 261–265.
Poehlman (1987) *Breeding Field crops*. pp. 139–142.

*Primary Examiner*—Gary Benzion
*Attorney, Agent, or Firm*—Leydig, Voit & Mayer, Ltd.

[57] ABSTRACT

The present invention relates to the field of producing hybrid seeds, and specifically relates to the application of certain cloned nuclear restorer genes that are active in reversing cytoplasmic male sterile systems. In particular, the present invention relates to: certain polynucleotide sequences that hybridize to nuclear restorer genes of plants, vectors, organisms, seeds, plant cells, and plants that comprise such polynucleotide sequences; a novel method for the production of hybrid seed that uses the aforementioned polynucleotide sequence; and a second novel method for the production of variant cytoplasmic male sterile factors.

16 Claims, 2 Drawing Sheets rf2-m8122
Mu1 COPY NUMBER REDUCTION AND COSEGREGATION 3.4 kb→
EcoRI
HindIII

COSEGREGATION OF pRf2 AND rf2-m8122

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
CTTTTCCTCT TCTGATGTAT GCCTGGAAAG TTGGCCCTGC TTTGGCATGT GGAAATACTC        60
TCGTGCTCAA GACTGCTGAA CAAACCCCTC TATCGGNTTT GTATATCTCC AAATTGTTGC       120
ATGAGGCTGG ACTACCTGAG GGTGTTGTGA ATGTCGTTTC TGGTTTTGGN CCTACTGCTG       180
GTGCTGCTCT TGCTAGTCAC ATGGATGTTG ATAAGATCGC ATTACTGGA TCTACCGATA        240
CTGGAAAAAT TATTCTCGAG TTGGCTGCAA AGAGCAACCT TAAGACAGTG ACACTGGAGT       300
TAGGAGGAAA GTCCCCTTTC ATCATATGGA CGAAGCTGAT GTTTGGACCA GCTNTTGGAG       360
CTTGNGCANC TTGGCCTGTN CTTTTACCAG GANAATGCTG TA                          402
```

( 2 ) INFORMATION FOR SEQ ID NO:2:

( i ) SEQUENCE CHARACTERISTICS:
        ( A ) LENGTH: 133 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Phe Pro Leu Leu Met Tyr Ala Trp Lys Val Gly Pro Ala Leu Ala Cys
 1               5                  10                  15

Gly Asn Thr Leu Val Leu Lys Thr Ala Glu Gln Thr Pro Leu Ser Xaa
            20                  25                  30

Leu Tyr Ile Ser Lys Leu Leu His Glu Ala Gly Leu Pro Glu Gly Val
        35                  40                  45

Val Asn Val Val Ser Gly Phe Gly Pro Thr Ala Gly Ala Ala Leu Ala
    50                  55                  60

Ser His Met Asp Val Asp Lys Ile Ala Phe Thr Gly Ser Thr Asp Thr
65                  70                  75                  80

Gly Lys Ile Ile Leu Glu Leu Ala Ala Lys Ser Asn Leu Lys Thr Val
                85                  90                  95

Thr Leu Glu Leu Gly Gly Lys Ser Pro Phe Ile Ile Trp Thr Lys Leu
            100                 105                 110

Met Phe Gly Pro Ala Xaa Gly Ala Xaa Ala Xaa Trp Pro Val Leu Leu
        115                 120                 125

Pro Gly Xaa Cys Cys
    130
```

( 2 ) INFORMATION FOR SEQ ID NO:3:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

```
CTTTTCCTCT TCTGATGTAT GCCTGGAAAG TTGGCCCTGC TTTGGCATGT GGAAATACTC        60
TCGTGCTCAA GACTGCTGAA CAAACCCCTC TATCGGCTTT GTATATCTCC AAATTGTTGC       120
ATGAGGCTGG ACTACCTGAG GGTGTTGTGA ATGTCGTTTC TGGTTTTGGN CCTACTGCTG       180
GTGCTGCTCT TGCTAGTCAC ATGGATGTTG ATAAGATCGC ATTACTGGA TCTACCGATA        240
```

```
CTGGAAAAAT  TATTCTCGAG  TTGGCTGCAA  AGAGCAACCT  TAAGACAGTG  ACACTGGAGT        300

TAGGAGGAAA  GTCCCCTTTC  ATCATATGGA  CGAAGCTGAT  GTTTGGACCA  GCTGTTGGAG        360

CTTGNGCANC  TTGGCCTGTN  CTTTTACCAG  GANAATGCTG  TA                           402
```

NUCLEAR RESTORER GENES FOR HYBRID SEED PRODUCTION

GOVERNMENT SUPPORT

This invention was made with government support under Grant Nos. GAM9001136, AMD9201761, and 9400901, all awarded by the United States Department of Agriculture. The United States Government has certain rights in the invention.

TECHNICAL FIELD OF THE INVENTION

The present invention relates to the field of producing hybrid seeds, and specifically relates to the application of certain cloned nuclear restorer genes that are active in reversing cytoplasmic male sterile systems.

BACKGROUND OF THE INVENTION

In plants, the best first filial ($F_1$) hybrids have a substantial yield advantage over the best open-pollinated varieties or inbred lines. This yield advantage of a hybrid over its parents is termed heterosis. The degree of heterosis observed varies among species; however, as a general rule, it is high among cross-pollinated species, such as maize and sunflower, and typically lower among self-pollinated species, such as soybean and wheat. Indeed, providing the generation of producing the hybrid seed is sufficiently inexpensive, the manufacture and sale of hybrid seed forms the basis of a significant agricultural industry. For example, hybrid varieties of corn (a/k/a maize) largely supplanted open-pollinated varieties at least from the 1940's because of the ease of generating hybrid maize seed coupled to the startling improvement in yield and other agronomic traits when hybrid varieties were used.

To obtain $F_1$ hybrid seed, it is necessary to cross two inbred parents. Although it is possible to do this via controlled pollinations (i.e., fertilizations) flower by flower, such an approach is labor intensive and, thus, very expensive. Only high-value crops such as ornamental flowers and the like could absorb such costs of production.

In maize, an intermediate course historically has been taken: It is possible to grow two maize parents in isolation from other maize pollen sources, detassel (emasculate) the "female" parent plants and let the "male" parent produce pollen and fertilize via standard cross-pollination. The designation of male and female may be considered arbitrary in this context because wild-type maize is monecious, having both male and female flowers on each plant. However, there often are commercially significant reasons for selecting one parent rather than the other as female or male. For example, a preferred female has ample seed production, whereas a preferred male has ample pollen production. Seed harvested from the female parent is therefore derived from the cross of the female by the male and thereby produces hybrid seed.

This detasseling approach for emasculating the female plant is how hybrid seed was produced until the advent of cytoplasmic male sterility ("CMS") systems. CMS had the advantage of not requiring detasseling because the products of CMS genes caused ill-formed, non-productive anthers. The system works as follows: Factors resident in the plant cell's cytoplasm have been found to cause male sterility (see Laughnan et al., *Ann. Rev. Genet.*, 17, 27–48 (1983)). Such factors have been determined to be associated with mitochondria, indeed to be mitochondrial genes, and thus are inherited maternally. Accordingly, a female line can be established that is cytoplasmic male sterile, thus it cannot cross- or self-pollinate. By crossing such a female line with pollen from another line that includes nuclear factors capable of reversing the male sterility in the $F_1$, fertile hybrid seed can be generated without the requirement of detasseling the female plants.

A maize variety can be converted into a CMS line by crossing it (as male) to a known cytoplasmic male sterile line and then backcrossing it (as female) to the initial inbred line. Of course, the CMS-converted line is male sterile, so it must be maintained by crossing by the original inbred line (called a maintainer). To make hybrid seed, one merely grows the CMS-converted inbred line and a second inbred line in isolation. Because the CMS-converted line is male-sterile, it is not necessary to detassel it. If the second inbred line is also CMS-converted, the hybrid progeny will also be male sterile, resulting in infertile plants that would have limited economic value. To overcome this difficulty, nuclear restorer genes are used. Most male sterile cytoplasms are restored to fertility in a succeeding generation when combined with certain nuclear genes, called restorers. If the second inbred line carries one of these restorers, then the $F_1$ will be male-fertile, and, potentially, provide economic value.

In maize (*Zea mays L.*), there are three major groups of male-sterile cytoplasms: S (USDA), C (Charrua), and T (Texas), in addition to the N or normal male-fertile cytoplasm. These cytoplasms can be classified by the different nuclear genes that suppress their associated male-sterile phenotype, thereby allowing normal pollen development (see Laughnan et al., supra), by mitochondrial DNA restriction endonuclease profiles (see Pring et al., *Genetics*, 89, 121–136 (1978)), and by characteristic polypeptide patterns resulting from $^{35}$S-methionine incorporation by isolated mitochondria (see Forde et al., *Proc. Nat'l. Acad. Sci. USA*, 75, 3841–3845 (1978)).

The normal N cytoplasm yields fertile plants in either the presence or absence of all known nuclear backgrounds, whereas the male-sterile C, S, and T cyto-plasms only produce fertile plants in nuclear backgrounds carrying the appropriate restorer genes. These nuclear-encoded fertility-restorer genes compensate for cytoplasmic dysfunctions that are phenotypically expressed during microsporogenesis and/or microgametogenesis. Plants carrying S and C cytoplasm are restored to fertility by single dominant alleles of the rf3 and rf4 loci, respectively. The rf4 locus maps to chromosome 8, approximately 2 cM from the RFLP ("restriction fragment length polymorphism") marker NP1114A (Sisco, *Crop Sci.*, 31, 1263–1266 (1991)). Preliminary evidence suggests that the rf3 locus is flanked by whp and bn117.14 on chromosome 2 L (T. Kamps et al., *Maize Genet. Coop. Newsl.*, 66, 45 (1992)). In contrast to S and C cytoplasm, plants with T cytoplasm are restored to fertility by the dominant alleles of two loci, rf1 and rf2 (Laughnan et al., supra), which are located on separate chromosomes. The rf1 locus is flanked by umc97 and umc92 on chromosome 3 and the rf2 locus is flanked by the umc153 and sus1 on chromosome 9 (Wise et al., *Theor. Appl. Genet.*, 88, 785–795 (1994)).

The mode of restoration of T cytoplasm is sporophytic; the genetic constitution of the diploid sporophytic anther tissue, rather than the haploid, gametophytic pollen grain, determines pollen development. Therefore, a T-cytoplasm plant that is heterozygous for both restorer gene loci (Rf1/rf1, Rf2/rf2), will produce all normal pollen even though only one-fourth of the pollen grains carry both Rf1 and Rf2 (Laughnan et al., supra).

Maize is not alone in having a CMS phenomenon. Other species also have approaches to engineering male sterility, which include a variety of cytoplasmic male sterility (CMS) and fertility restoration systems that have been well characterized at the genetic and molecular levels. Some examples of these CMS systems include petunia (Nivison et al., *Plant Cell*, 1, 1121–1130 (1989)), common bean (Janska et al., *Genetics*, 135, 869–879 (1993)), *Brassica napus* (Singh et al., *Plant Cell*, 3, 1349–1362 (1991)), sunflower (Laver et al., *The Plant Journal*, 1, 185–193 (1991)), sorghum (Bailey-Serres et al., *Theor. Appl. Genet.*, 73,252–260 (1986)), oats (Mann et al., *Theor. Appl. Genet.*, 78, 293–297 (1989)), S-cytoplasm maize (Schardl et al., *Cell*, 43, 361–368 (1985)), and T-cytoplasm maize (Levings, *Plant Cell*, 5, 1285–1290 (1993)). Cytoplasmic male sterility in petunia, beans, Brassica, and S-cytoplasm maize can be restored to fertility by single dominant nuclear genes. In contrast, T-cytoplasm maize is restored by the combination of dominant alleles of two unlinked, nuclear restorer genes, rf1 and rf2 (Laughnan et al., supra).

Most of the research on CMS systems has focused on the characterization of novel open reading frames in their respective mitochondrial genomes, i.e., the cytoplasmic component of CMS. Such research has revealed that, although each open reading frame is unique, all known such open reading frames appear to have large hydrophobic domains (Dewey et al., *Proc. Nat'l. Acad. Sci. USA*, 84, 5374–5378 (1987)). In T-cytoplasm maize, the unique mitochondrial gene, T-urf13, is associated with the CMS (Wise et al., *Proc. Nat'l. Acad. Sci. USA*, 84, 2858–286 (1987a)) and toxin sensitivity traits (Huang et al., *EMBO J*, 9, 339–247 (1990)). T-urf13 encodes a 13 kDa mitochondrial polypeptide (URF13) (Wise et al., *Plant Mol. Biol.*, 9, 121–126 (1987b)), located in the mitochondrial membrane (Dewey et al., supra (1987)). It is also known that this polypeptide is not synthesized by deletion mutants (Dixon et al., *Theor. Appl. Genet.*, 63, 75–80 (1982)), and is truncated in a T4 frameshift mutant (Wise et al., supra (1987b)). The URF13 protein binds to fungal pathotoxins (Braun et al., *Plant Cell*, 2, 153–161 (1990)) and appears to span the mitochondrial membrane in oligomeric form (Korth et al., *Proc. Nat'l. Acad. Sci. USA*, 88, 10865–10869 (1991)).

The abundance of the URF13 protein is reduced by approximately 80% in plants carrying Rf1 and Rf2 (Dewey et al., supra (1987)). Analysis of T-urf13 specific transcripts in restored and nonrestored nuclear backgrounds revealed an additional 1.6 kb transcript in T-cytoplasm plants restored to fertility (Kennell et al., *Mol. Gen. Genet.*, 210, 399–406 (1987)). The modification of T-urf13 transcription and the concurrent reduction of the URF13 protein appears to require the action of only Rf1 and not Rf2 (Dewey et al., supra (1987)); however, other modifiers also appear to have an effect on T-urf13 transcription depending on the nuclear background (Kennell et al., supra). Little is known about Rf2 except that, in addition to Rf1, it is essential for pollen restoration.

T cytoplasm was used predominantly in the late 1960's because of its reliability to cause male sterility in the female plants. The other CMS systems of maize, the C and S cytoplasms, tended to "break down" in the field, allowing some self-fertilization by the female plants or failing to restore completely. Thus, approximately 85% of the U.S. hybrid maize seed had a genetic background that included T cytoplasm until the 1970 epidemic of southern corn leaf blight (Pring et al., *Ann. Rev. Phytopathol.*, 27, 483–502 (1989)). Never before or since has a major crop in the United States had so nearly uniform a genetic background underlying the various hybrids on the market at that time. Subsequent to the 1970 epidemic, it was determined that maize that carries T cytoplasm is highly sensitive to the host-selective toxin (T toxin) produced by race T of the fungus *Cochliobolus heterostrophus* Drechsler (asexual stage *Bipolaris maydis* Nisikado and Miyake), which is the causal organism of southern corn leaf blight. See Comstock et al., *Phytopathology*, 63, 1357–1361 (1973). T cytoplasm-carrying maize was also found to be highly sensitive to the host-selective toxin (Pm toxin) produced by another fungus *Phyllosticta maydis*, Army and Nelson, which causes yellow leaf blight (Yoder, *Phytopathology*, 63, 1361–1366 (1973)). Accordingly, the major seed producers have resorted to a system of selection that involves using different CMS systems (including T). Hybrid seed produced using these different systems is mixed together prior to being sold to farmers. In this way, any given farmer's fields are sown with seeds that include varying combinations of, for example, T, C, S, and N cytoplasms produced either via CMS (in the case of T, C, and S) or detasseling (in the case of N).

A focus of research since the 1970's has been to develop alternative genetic approaches to emasculating plants for the purpose of hybrid seed production. This effort is due in part to the interest of not having an homogeneous genetic background in crops. One such system, invented by Marc Albertsen for Pioneer Hi-Bred International, Inc., involves using a genetic male sterility system located in the nuclear genome. There are many such mutations available in a given plant species, including maize (Albertsen et al., *Can. J. Genet. Cytol*, 23, 195–208 (1981)). The Pioneer system is based on a molecular clone of the nuclear maize gene that confers male sterility, and is predicated, at least in part, on earlier analogous work on Arabidopsis (see Aarts et al., *Nature*, 363, 715–717 (1993)). The difficulty of this approach centers on the maintenance of the male sterile ("ms") line. To overcome this difficulty, Albertsen has proposed the creation of an inbred line that is homozygous for a mutant allele of the ms gene. This line is proposed also to carry a genetically engineered construct that has an inducible promotor that will allow expression of a wild-type coding region of the ms gene. To maintain the inbred line, it will be grown by itself in isolation, sprayed with the inducer (which turns on the wild-type ms gene), and allowed to self- and sib-pollinate. To make hybrid seed the inbred line will be grown in isolation with a second inbred line in the absence of inducer, thus the first line will be male sterile and hybrid seed will be harvested from it. As used in the farmers' fields, the $F_1$ should be male fertile because the second inbred line of the cross will carry a wild-type allele of the ms gene, making the $F_1$ heterozygous, and thus fertile.

Another system designed to augment the prior CMS systems was developed by Leemans et al. for Plant Genetic Systems ("PGS"), and was disclosed in *Nature*, 347, 737–741 (1990). The PGS system is based on an RNase gene that is driven by a tapetum-specific promotor. The RNase is therefore active only in the anthers where it kills the tapetum, which are structures that normally nourish the pollen. The result is male-sterile plants. This system results in dominant male-sterility. Hence by introducing (via backcrossing or transformation) this system into an inbred line, one generates a male sterile inbred line. However, the mutation is heterozygous and therefore when the male-sterile line is crossed by a normal line, the progeny segregate for ms and N (i.e., normal). To overcome this difficulty, the Plant Genetic Systems method uses a genetic construct whereby a herbicide resistance gene is linked tightly to the ms gene. In practice, the ms line is crossed by the normal progenitor line. The resulting segregating progeny are grown in isolation with a second inbred line. The rows that carry the first inbred line are sprayed with an herbicide. The male fertile progeny die, leaving only the ms inbred plants from which hybrid seed can be harvested.

In view of the above, it is apparent that a difficulty encountered in the prior art is that the T cytoplasm male sterility approach to hybrid seed production presents a high risk of certain fungal diseases in plants derived therefrom. Other CMS systems currently available offer far less efficiency relative to the T cytoplasm system, albeit no epidemics have as yet been associated with the non-T systems. Yet other non-CMS systems are available, but require extra manipulations of inducer genetic elements and involve increased economic and possibly environmental costs relating to the use of inducing agents, for example.

Accordingly, it is an object of the present invention to provide new materials and methods that will allow one to produce hybrid seeds from a female line having novel cytoplasmic male sterility factors. It is a further object of the present invention to provide new plants having novel cytoplasmic male sterility factors and/or plants producing seeds having novel cytoplasmic male sterility factors. It is yet a further object of the present invention to provide the isolated genes and gene products responsible for the cytoplasmic male sterility factors in plants.

These and other objects and advantages of the present invention, as well as additional inventive features, will be apparent from the description of the invention provided herein.

SUMMARY OF THE INVENTION

It has been discovered that nuclear restorer genes may be isolated and used for the production of new varieties of CMS systems. Accordingly, an enriched or substantially isolated nucleic acid comprising a nucleotide sequence that encodes a nuclear male fertility restorer gene, in particular, has been isolated. Vectors, organisms, seeds, plant cells, and plants comprising such a nucleic acid have been discovered as well.

Moreover, another embodiment of the present invention relates to a method for the production of hybrid seed, comprising the steps of: (a) constructing a nucleic acid comprising a nucleotide sequence that encodes a nuclear male restorer gene; (b) inserting the nucleic acid into a plant cell; (c) establishing a first plant from the plant cell having and expressing the nucleic acid; and (d) cross-pollinating a second plant by the first plant, wherein the action of the male fertility restorer gene contained in the first plant compensates for the cytoplasmic male sterility factor in the second plant.

Yet a further embodiment of the present invention relates to a method for the production of variant cytoplasmic male sterility factors, comprising the steps of: (a) constructing a nucleic acid comprising a nucleotide sequence that encodes a male fertility restorer gene product; (b) inserting the nucleic acid into a plant cell; (c) culturing the cell, thereby generating a first plant; and (d) selecting a second plant that is cytoplasmic male sterile, which when crossed by the first plant produces fertile seed.

DETAILED DESCRIPTION OF THE PREFERRED EMBODIMENTS

Figure 1A:
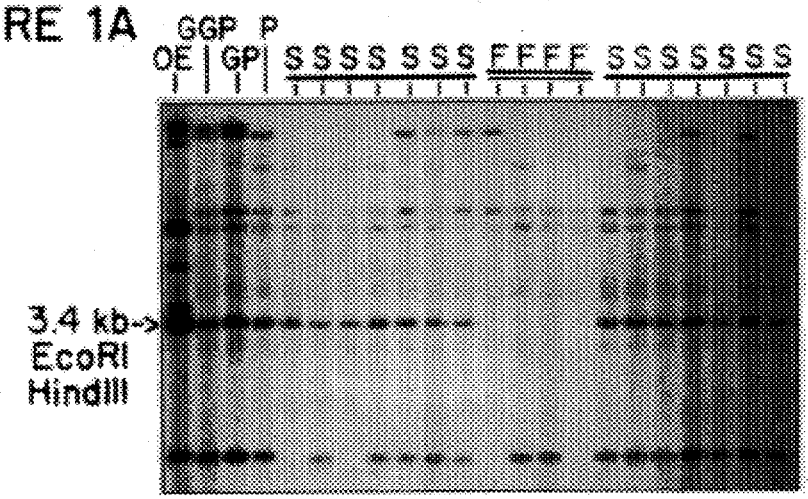
FIG. 1A and FIG. 1B display photographs of autoradiograms of the same Southern blot containing restriction endonuclease-cut DNA from male sterile and male fertile sibs, wherein the blot depicted in FIG. 1A was probed with a radiolabeled Mu-1 molecular probe, and the blot depicted in FIG. 1B was probed with radiolabeled rf2 probe #1.

The present invention provides certain genetic sequences relating to restoration of male fertility in plants, and further provides methods for the use of such sequences for the generation of new varieties of cytoplasmic male sterility systems, which are useful in the production of hybrid seed. Accordingly, the present invention is also embodied in a novel method for the production of hybrid seed.

In particular, the present invention provides an enriched or isolated nucleic acid comprising a nucleotide sequence that encodes a nuclear restorer gene product of a plant, or a portion thereof, the action of which is to restore male fertility to a plant having a cytoplasmic male-sterility (CMS) trait. As used herein, the CMS trait is considered to be the direct result of certain CMS factors, which may actually be a single or multiple genes acting to produce the CMS trait. A nuclear restorer gene product may be a polypeptide or an RNA molecule. The nuclear restorer gene product, as just stated, is involved in restoring male fertility by action on mitochondrial or chloroplast functions, although the present invention is derived from the nuclear genome.

Genes in maize that effect restoration of cytoplasmic male sterility have been named "rf". See Levings et al., *Cell*, 56, 171–179 (1989). Similar effects have been noted in a range of other plant species, as noted in the Background, and are believed to be applicable to a broad range of plants including such important agricultural crops as soybean, alfalfa, wheat, sorghum, beet, various vegetables including cucumber, tomato, peppers, and the like, various trees including apple, pear, peach, cherry, redwood, pine, oak, and the like, and various ornamentals. Indeed, in view of the fundamental nature of the activity of the present invention, the present invention is viewed as applicable to any sexual reproducing plant.

The term "nucleic acid" refers to a polymer of DNA or RNA, i.e., a polynucleotide, which can be single- or double-stranded, and can optionally contain synthetic, nonnatural, or altered nucleotides. Any combination of such nucleotides can be incorporated into DNA or RNA polymers. The nucleic acid is "enriched" in that the concentration of the material is at least about 2, 5, 10, 100, or 1000 times its natural concentration, for example, advantageously 0.01% by weight, preferably at least about 0.1% by weight. Enriched preparations of about 0.5%, 1%, 5%, 10%, and 20% by weight are also contemplated. A polynucleotide is "isolated" in that the material has been removed from its original environment, e.g., the genome of a plant, presuming that it is naturally occurring. Thus, describing the polynucleotide of the present invention as "substantially isolated" reflects the increase in concentration of the polynucleotide of interest with respect to other polynucleotides, as when, for example, the polynucleotide of interest is taken from a plant (which, in the case of maize, has a complement of three million kb) and is placed or cloned into a bacteriophage (which, in the case of lambda ("λ") has a complement of 50 kb), resulting in a 60,000-fold increase in concentration of the inventive polynucleotide sequence with respect to the total amount of DNA in the bacteriophage in which it is placed. It is also advantageous that the nucleic acids be in purified form, or substantially purified form, wherein "purified" does not mean absolute purity but rather relative purity, wherein, for example, the nucleic acids of the present invention are isolated in a laboratory vessel in a mixture of other nucleic acids, such as portions of a vector or other molecules associated with genetic engineering.

Preferably, the enriched or substantially isolated nucleic acid hybridizes under at least moderately stringent hybridization conditions to a second nucleic acid that includes nucleotide sequences specific to an rf gene, or substantial portions thereof; more preferred, the nucleic acid hybridizes under the aforementioned conditions to a second nucleic acid that includes nucleotide sequences specific to the rf1 or rf2 gene, or substantial portions thereof; yet more preferred the selected nucleotide sequence are specific to the rf2 gene.

Stringency of hybridization is a term of art that refers to the conditions used for a hybridization reaction whereby complementary single strands of nucleic acid join to one another to form double-stranded nucleic acid with some degree of mismatch, the degree of which is a function of the stringency used. In particular, the stringency will depend upon the size and composition of the strands of nucleic acid that are caused to react, the degree of mismatching allowed, the desired cross reactivity, and the like. The degree of stringency can be affected by the ionic conditions employed and temperature, among others, as is well known in the art. Sambrook et al., *Molecular Cloning: A Laboratory Manual* (2d ed., 1989).

As used in the context of the present invention, the specified stringency of hybridization in part define the inventive nucleic acid. Accordingly, the hybridization conditions are designed suitably to be at least moderately stringent or stringent. In the former case, suitable conditions of salt, temperature, reaction mixture, and size of nucleic acid reactants are set in accordance with conventional knowledge to provide from about 45% to about 70% mismatch of the sequence of nucleotides of the nucleic acid. Preferably, moderately stringent hybridization conditions are set to provide from about 55% to about 75% mismatch; and more preferably, such conditions are set to provide from about 60% to about 70% mismatch. In the latter case, suitable conditions for hybridization are set in accordance with conventional knowledge to provide from about 10% to about 40% mismatch. Preferably, stringent hybridization conditions are set to provide from about 20% to about 40% mismatch; and more preferably, such conditions are set to provide from about 30% to about 40% mismatch. By mismatch, it is meant the degree to which non-complementary base pairs are found opposite one another in otherwise duplex nucleic acid, thereby forming bubble structures and causing the melting temperature of the duplex to be lower as compared to 100% matched duplex of the same length and base composition.

Four loci of the nuclear restorer (rf) genes of maize have been described in the technical literature (for example, see Levings et al., supra), and have been further elucidated by work disclosed herein. The rf loci affect the capability to restore male fertility when certain cytoplasmic genes are operating or not operating. The names of the known loci are rf1, rf2, rf3, and rf4. Plants having dominant rf genes (recited as Rf) are usually identified because the anthers are fully formed and functional in the presence of cytoplasmic male sterility factors.

As noted above, with respect to the T cytoplasm, both rf1 and rf2 must have dominant alleles present to overcome the sterility factors provided by the T CMS system. Accordingly, a seedling must be at least heterozygous dominant for both loci before it counteracts a CMS T phenotype. Similarly, rf3 and rf4 have been identified as having analogous restoring functions in the, respectively, C and S CMS systems. The existence of the various rf genes involved in the restoration function suggests that the rf genes or a subset thereof may represent a gene family, wherein the members are related to an ancestral locus that duplicated and diverged in sequence at least once over evolutionary time. The importance of this observation and hypothesis is that the identification of one nucleic acid sequence specific to one of the rf genes, which is disclosed herein, may provide probes therefrom for the identification and isolation of other rf genes.

The present invention is also directed to a nucleic acid as described hereinabove that is flanked by regulatory-directed nucleic acid. Preferably, such regulatory-directed DNA is specific to plants, fungi, and bacteria. More preferably, such regulatory-directed nucleic acid is specific to a plant or plants, such as one of the aforementioned or other suitable agricultural plants. As noted above, the present invention provides, inter alia, plant varieties that differ from wildtype by the inclusion of nucleic acids in accordance with the present invention. In this context, regulatory sequences of nucleic acid that direct the activity of a particular gene to occur at a point in or period of the development of the plant and/or direct the development of the male sex organs of the plant, such as the anther, may be affixed upstream or downstream of the rf gene of interest. Such regulatory DNA sequences are known to those of ordinary skill in the art.

The nucleic acid of the present invention can be isolated from any suitable plant having the appropriate genotype. As noted in the Background section above, all sexual plants have anthers, which in maize becomes incorporated in the tassel structure. Certain deficiencies of mitochondria have been shown to interfere with anther structure and, concomitantly, with pollen production. Because mitochondria are the energy providers to a cell, such deficiencies can be severe. Thus, such effects on male fertility can only be reversed if the cells can provide a means to reverse the mitochondrial deficiencies. As exemplified below, it is now known that at least one nuclear restorer gene (rf2) that counteracts cytoplasmic male sterility is isolable from a cDNA library derived from the mRNA present in tassel tissue. Construction of such a cDNA library and the appropriate harvesting of the tassel tissue was accomplished using conventional knowledge and techniques, using bacteriophage lambda as host for the cDNA library.

The isolated rf2 cDNA sequence has a high degree of homology to aldehyde dehydrogenase from various sources, including cows and rats. Aldehyde dehydrogenase is a rather mundane "housekeeping" protein that acts in the mitochondria or cytosol. It is also an enzyme known to provide a detoxifying function, as utilized in the liver of a mammal. Such mechanisms can be foreseen to work and function in the same manner in essentially all plants, albeit the detoxifying function would necessarily take place in the absence of a liver. This is particularly supported by the fact, exemplified below, that the maize rf2 gene is highly conserved with respect to the same enzyme in cows, which, of course, are very distant from plants on the evolutionary scale.

Accordingly, preferred nucleic acids of the present invention are isolated from any suitable sexual-reproducing plant. Such plants are either monocotyledonous or dicotyledonous, including maize, wheat, barley, rice, oats, rye, soybean, rapeseed, canola, cotton, safflower, peanut, palm, sorghum, sunflower, tomato, cucumber, and ornamental flowers. The more preferred plant that the rf genes are derived from is maize.

The present invention also provides a nucleic acid of which the nucleotide sequence thereof hybridizes to the cDNA having the sequence of SEQ ID NO:1 or SEQ ID NO:3, or a sequence complementary thereto, under at least moderately stringent conditions. SEQ ID NO:1 and SEQ ID NO:3 encompass the same number of nucleotides, wherein SEQ ID NO:1 includes the entire sequence of SEQ ID NO:3, which includes two fewer nucleotide positions occupied by N, as provided in the SEQUENCE LISTING below. A preferred nucleic acid according to the present invention hybridizes to SEQ ID NO:1 only under stringent hybridization conditions. A more preferred enriched or isolated nucleic acid of the present invention comprises a nucleotide sequence selected from the group consisting of SEQ ID NO:1, a sequence complementary thereto, and a substantially equivalent sequence. SEQ ID NO:1 is a partial sequence (402 bases sequenced out of a total of about 1200 bases) of the cDNA derived from the maize rf2 gene, the identification and isolation of which are disclosed in Examples 1 and 2. SEQ ID NO:1 may not be a full-length cDNA (i.e., including the complete complement of the rf2 mRNA) because, as compared to the evidently homologous aldehyde dehydrogenase gene sequences disclosed at Example 4, approximately 500 bp of the rf2 message is missing. Nevertheless, one of ordinary skill in the art certainly recognizes that SEQ ID NO:1 or SEQ ID NO:3 provides sufficient rf2 sequence information to provide probes for the identification and cloning of any rf2 genes or to any gene that is substantially homologous to rf2 in sequence such that the rf2 probe hybridizes under moderately to extremely stringent hybridization conditions, as discussed hereinabove.

A "substantially equivalent" sequence is a sequence that, with respect to SEQ ID NO:1, for example, varies from the SEQ ID NO:1 sequence by one or more substitutions, deletions, or additions, the effect of which does not result in an undesirable functional dissimilarity between the two sequences. Thus, conventionally known "neutral mutations," which have no impact on the resultant amino acid sequence, are fully included in this definition. In addition, conventionally known "conservative mutations," which does change some of the resultant amino acids for those of approximately equivalent size, shape and charge characteristics, such as, for example, an isoleucine or glycine for a leucine, but such exchange has little or no deleterious impact on the functioning of the resultant protein with respect to the progenitor protein. In other words, the polypeptide that results from the substantially equivalent sequence has the activity characteristic of the rf2 gene product. A difference in sequence at the amino acid level will be understood to include amino acid differences, which range from a single amino acid substitution, deletion, or insertion to a number of amino acid substitutions, deletions, and/or insertions, wherein the resulting polypeptide is still recognizable as related to the rf2 protein as well as those amino acid sequence differences, which result in a larger polypeptide, such as a precursor protein, a complete mature protein, or a truncated protein. Accordingly, even nonconservative exchanges of amino acids with respect to the progenitor protein may be included in the embodiment of the present invention so long as the rf gene product activity remains substantially unchanged.

The enriched or isolated nucleic acid which comprises the nucleotide sequence of SEQ ID NO:1 is most preferred. The present inventive nucleic acid may be identified for enrichment or isolation by hybridization to any subfragment of SEQ ID NO:1 of at least 20 nucleotides under stringent hybridization conditions as described in Sambrook et al., *Molecular Cloning: A Laboratory Mammal* (2d ed., 1989). Accordingly, this invention encompasses the entire sequence of the rf2 gene and fragments thereof, which have been generated by any suitable technique, such as by restriction enzyme digestion of chromosomal or plasmid DNA, or by synthesis, and which may be either DNA or RNA.

In addition to the methods recited in Example 1 for the identification and isolation of nuclear restorer genes and related nucleic acids of the present invention, other methods may be used alternatively, such as, inter alia, chromosome walking and heterologous probe selection.

Chromosome walking is a particularly useful technology that can facilitate the molecular isolation of any mapped gene (Bender et al., *J. Mol. Biol.*, 168, 17–338 (1983)) and has been found to be particularly useful with plants that have a relatively small genome size, such as that of Arabidopsis. Meyerowitz, in *Methods in Arabidopsis Research* (Koncz et al., eds., World Scientific, Singapore, 1992), pages 100–118). In addition, five YAC libraries, representing 28 genome equivalents, exist for this species. Gibson and Somerville, in *Methods in Arabidopsis Research* (supra). Several Arabidopsis genes have been cloned via this strategy (Yanofsky et al., *Nature*, 346, 35–39 (1990); Giraudat et al., *Plant Cell*, 4, 1251–1261 (1992); and Arondel et al., *Science*, 258, 1353–1354 (1992)). This technique is useful, of course; in species of larger genome size as well, such as maize.

A chromosome walk is initiated by identifying from a library of large DNA fragments the specific fragment(s) that contain sequences homologous to a restriction fragment length polymorphism (RFLP) marker or some other marker that is closely linked to the target gene. Typically, the library of DNA fragments is maintained as yeast artificial chromosomes, i.e., YACs (Burke et al., *Science*, 236, 806–811 (1987)), although cosmids, P1 phage or λ phage have been used. Single copy sequences from the termini of YACs that contain sequences homologous to a starting RFLP are then used as hybridization probes to isolate overlapping DNA fragments. This process is repeated until the entire chromosomal region, from the starting RFLP marker to beyond the target gene, has been cloned as a contiguous segment (a "contig"). Typically, the contig is oriented by mapping DNA sequences from the growing contig to the genetic/RFLP map. Similarly, the endpoint of the walk is established by demonstrating that the contig contains DNA sequences from both sides of the target gene. For both of these operations, DNA sequences from the contig must be genetically mapped. The efficiency of this mapping can be greatly increased by selecting a population of plants that have a high probability of carrying recombination breakpoints in the region defined by the contig. Such a mapping population is established by selecting plants that carry a recombination breakpoint between two visible genetic markers that flank the interval to be walked. The precision of the mapping increases proportionally with the number of genetic recombinants. The greater the precision of this mapping, the smaller the uncertainty associated with the positioning of the target gene on the contig. Once the target gene has been localized in the contig to as small an interval as the mapping population permits, the target gene is identified from the interval via its ability to complement genetically the mutant phenotype. The ability of a sequence to complement the mutant phenotype is assayed by transforming plants homozygous for a mutant allele of the target gene. Alternatively, comparisons between wildtype and mutant sequences can also identify the target gene from the interval.

Other technologies for gene isolation in Arabidopsis and other plants include genomic subtraction, and transposon and T-DNA tagging. Genomic subtraction requires the availability of strains having deletions of the target gene (Strauss and Ausubel, *Proc. Natl. Acad. Sci. USA*, 87, 1889–1893 (1990); Sun et al., *Plant Cell*, 4, 119–128 (1992)); however, such deletions are not available for rf2, for example. A transposon tagging system in Arabidopsis has recently become available. The success in tagging and cloning a petunia gene using a heterologous maize transposon (Chuck et al., *Plant Cell,* 5, 371–378 (1993)) provided the direction to extend this technique to Arabidopsis, and further supports the view that this technique is amenable to tagging virtually any plant with heterologous (Dean et al., *Plant J.,* 2, 69–81 (1992); Grevelding et al., *Proc. Natl. Acad. Sci. USA,* 89, 6085–6089 (1992); Swinburne et al., *Plant Cell,* 4, 583–595 (1992); and Fedoroff and Smith, *Plant J.,* 3, 273–289 (1993)) and/or endogenous (Tsay et al., *Science,* 260, 342–344 (1993)) transposons. T-DNA tagging, another method to locate a gene, has been realized (Feldmann, *Plant J.,* 1, 71–82 (1991)) and is in wide use (e.g., Feldmann et al., *Science,* 243, 1351–1354 (1989); Herman et al., *Plant Cell,* 11, 1051–1055 (1989); Konz et al., *EMBO J.,* 9, 1337–1346 (1989); Kieber et al., *Cell,* 72, 427–441 (1993)). Additionally, having isolated at least one nuclear restorer gene, the nucleic acid thereof can be used whole or in parts (by sub-cloning fragments thereof) as a probe in heterologous systems. Preferably, such a technique requires that the stringency of the selective hybridization procedure by lowered, and then slowly raised, as is well known in the art.

Although T-DNA tagging, chromosome walking or heterologous probe selection can identify a DNA fragment that putatively contains the gene of interest, in each instance these DNA fragments must be confirmed by genetic complementation or some other means, which is fully disclosed in Examples 1 and 2. Although the methods of identification of a particular gene sequence has been described herein largely with reference to maize and Arabidopsis only, it is abundantly clear to one of ordinary skill that such methods may be adapted for gene identification in other species, particularly in the context of the present invention. Accordingly, the identification of the rf genes, and cloning and using thereof, is enabled hereby for any of the aforementioned sexual-reproducing plants, as well as other plants that have mitochondrial deficiency-derived phenotypes in need of amelioration or correction.

The nucleic acids of the present invention may be cloned in any suitable vector and the vector as constructed with nucleic acid insert of the present invention is used to transform or transfect any suitable host. *E. coli,* in particular *E. coli* TB-1, TG-2, DH5α, XL-BLue MRF' (Stratogene), SA2821 or Y1090, is a preferred host. A more preferred host is XL-Blue MRF' or TG-2. Suitable vectors include those designed for propagation and expansion or for expression or both. Constructs of vectors can be prepared, either circular or linear, to contain the entire rf gene nucleotide sequence or a portion thereof ligated to a replication system functional in a microorganism host, whether prokaryotic or eukaryotic. Suitable hosts include *E. coli, B. subtilis, P. aerugenosa, S. cerevisiae,* and *N. crassa.* Replication systems may be derived from ColE1, 2 mμ plasmid, lambda, SV40, bovine papilloma virus, or the like. In addition to the replication system and the inserted DNA, the construct usually will include one or more markers, which allow for selection of transformed or transfected hosts. Markers may include biocide resistance, e.g., resistance to antibiotics, heavy metals, etc., complementation in an auxotrophic host to provide prototrophy, and the like. A preferred cloning vector is selected from the group consisting of pUC18, pET11d, EMBL4, NM1149, pLZO3 and Lambda ZapII (Stratagene). Of course, it is well-appreciated in the art that nucleic acids may be cloned in suitable bacteriophage vectors, such as, for example λGT10.

The present invention provides expression vectors for the expression of such polypeptides. A preferred expression vector is one that comprises a nucleic acid comprising, as an insert, a nucleotide sequence that encodes a nuclear restorer gene product, preferably that of one of the aforementioned sexual-reproducing plants. A more preferred expression vector comprises a nucleic acid comprising a nucleotide sequence such as SEQ ID NO:1, a sequence complementary thereto, or a substantially equivalent sequence. The most preferred expression vector comprises a nucleic acid comprising the nucleotide sequence SEQ ID NO:1, and a vector as described above.

One skilled in the art will appreciate that any one of a number of expression vectors may be utilized in the context of the present invention with some degree of success, including, but not limited to, the following: pGEX2T, pATH11, pNH8A (Strategene, Inc., La Jolla, Calif.), pGL2 (Promega, Madison, Wis.), pEX2 (Boehringer Mannheim Biochemicals, Indianapolis, Ind.), and pMOSELlox (Amersham Corporation, Arlington Heights, Ill.). Additionally, vectors known in the art for expression in plant cells of exogenous DNA are contemplated for use within the context of the present invention as well.

Care should be taken to choose a vector that does not result in cytotoxic expression of the amino acid sequence encoded in the insert of the vector. For expression in microorganisms, the expression vector may differ from the cloning vector in having transcriptional and translational initiation and termination regulatory signal sequences and may or may not include a replication system that is functional in the expression host. The coding sequence is inserted between the initiation and termination regulatory signals so as to be under their regulatory control. Expression vectors may also include the use of regulatable promoters, e.g., temperature-sensitive or inducible by chemicals, or genes that allow for integration and amplification of the vector and insert DNA, such as tk, dhfr, metallothionein, and the like. Such controls, if incorporated into a plant, could allow for the efficient and economic production of hybrid seeds, for example, by promoting expression of the restorer gene function upon the advent of a triggering level of some inducing substance.

The vector can be used to express a dsDNA sequence, either isolated and cloned or synthesized, to obtain a precursor protein, which is subject to further manipulation by cleavage, a complete mature protein, or a fragment thereof by introducing the expression vector into an appropriate host, where the regulatory signals are functional in the host. The expression host is grown in an appropriate nutrient medium, whereby the desired polypeptide is produced and isolated from cells or from the medium, when the polypeptide is secreted. Where a host is employed in which the vector's transcriptional and translational regulatory signals are functional, then the rf gene DNA sequence may be manipulated to provide for the expression of the desired polypeptide in proper juxtaposition to the regulatory signals. The polypeptide products can be obtained in substantially pure form, particularly free of cellular debris, which may include such contaminants as, for example, proteins, polysaccharides, lipids, nucleic acids, viruses, bacteria, fungi, and combinations thereof, using methods well known in the art.

The nucleic acids described above may be used in a wide variety of ways, depending upon their size, their natural function, the use for which they are desired, and the degree to which they can be manipulated to modify their function. For example, nucleic acids of at least about 20 bases, more usually at least 50 bases, and usually not exceeding about 10000 bases, more usually not exceeding about 5000 bases, may serve as probes for the detection of the presence of a nuclear restorer gene or homologous nucleic acids in an organism. Such detection can provide information relating to whether manipulation of the plant with a particular nuclear restorer gene could provide an opportunity to generate new varieties of the plant, and provide novel methods for the efficient production of hybrid seed.

The method of detection involves duplex formation by annealing or hybridization of the oligonucleotide probe, either labeled or unlabeled, depending upon the nature of the detection system, with the DNA or RNA of an organism believed to produce the particular nuclear restorer gene. Usually this method of detection involves cell lysis, extraction of nucleic acids with organic solvents, precipitation of nucleic acids in an appropriately buffered medium, and isolation of the DNA or RNA. Alternatively, one can amplify specific sequences via polymerase chain reaction (PCR). The DNA may be fragmented by mechanical shearing or restriction endonuclease digestion. The nucleic acid may then be bound to a support or may be used in solution depending upon the nature of the protocol. The Southern technique (Southern, *J. Mol. Biol.*, 98, 503 (1975)) may be employed with denatured DNA by binding the single-stranded fragments, for example, to a nitrocellulose or nylon filter. RNA also may be blotted onto a filter (Thomas, *Proc. Natl. Acad. Sci. USA*, 77, 5201 (1980)). Preferably, the fragments are subjected to electrophoresis prior to binding to a support so as to enable the selection of various sized fractions. Alternatively, the assay may be accomplished on plant cells fixed to a substrate and permeabilized using methods known in the art, whereupon the hybridization procedure can be conducted to determine if a homologous gene to a particular nuclear restorer gene exists in the plant of interest, and/or if that plant is expressing RNA that is homologous to the nuclear restorer gene.

The oligonucleotide probes may be DNA or RNA, albeit usually they are DNA. The oligonucleotide sequence may be prepared synthetically or by cloning. Suitable cloning vectors are well-known to those skilled in the art. The oligonucleotide probe may be labeled or unlabeled. A wide variety of techniques exist for labeling DNA and RNA and include radiolabeling by nick translation, random priming, tailing with terminal deoxytransferase, or the like, where the bases employed are labeled, for example, with radioactive $^{32}$p. Other labels, that may be used include fluorophores, enzymes, enzyme substrates, enzyme cofactors, enzyme inhibitors, and the like. Alternatively, instead of using a label, which provides a detectable signal by itself or in conjunction with other reactive agents, ligands can be used to which receptors bind, where the receptors are labeled, such as with the above-indicated labels, to provide detectable signals by themselves or in conjunction with other reagents (see, e.g., Leary et al., *Proc. Natl. Acad. Sci. USA*, 80, 4045–4049 (1983)). The oligonucleotide probes are hybridized with the denatured nucleic acid, substantially intact or fragmented, or fractions thereof, under conditions of predetermined stringency, the practicalities of which have been discussed hereinabove.

In accordance with another aspect of the present invention, the nucleic acids disclosed herein are used in a method for the production of hybrid seed, comprising the steps of: (a) constructing a nucleic acid comprising a nucleotide sequence that encodes a male fertility restorer gene product; (b) inserting the nucleic acid into a plant cell; and (c) establishing a plant from the plant cell having and expressing the nucleic acid. The first plant, which is one of a line or variety of such plants, preferably can produce seeds, however, such seeds may or may not be fertile. Accordingly, the inventive method involves plant tissue culture techniques known in the art. Insertion of nucleic acids into a plant cell is accomplished by any suitable means, including cell bombardment, i.e., attaching the DNA to metallic pellets and blasting them through the plant's cell wall (Fromm et al., *Bio/Technology*, 8, 833–839 (1990); Gordon-Kamm et al., *Plant Cell*, 2, 603–618 (1990)), and, for the introduction of exogenous DNA to a dicotyledonous plant cell, insertion of the nucleic acid of the present invention into the Ti plasmid of Agrobacterium and adding suitable ingredients to promote transformation thereby (Horsch et al., *Science*, 222, 496–498 (1984); DeBlock et al., *EMBO J.*, 3, 1681–1689 (1984)). Other techniques are available for the introduction of exogenous DNA into a plant and/or a subset of its constituent cells, including electroporation, protoplast-mediated gene transfer, and silicon carbide crystal-mediated gene transfer. These various techniques are discussed in *Genetic Engineering News*, vol. 14, no. 4 (Feb. 15, 1994) pages 1, 3, and 24, and are generally known in the art. Accordingly, plants that include polynucleotide sequences of the present invention may be generated using tissue culture, thereby growing transformed or transvected cells into plants, or conventional gene transfer directly into a plant. This line of plants having and expressing the nucleic acid of the present invention, accordingly, is established using conventional breeding techniques.

Additionally, the inventive method further comprises (d) cross-pollinating a second plant by the first plant, wherein the second plant has a cytoplasmic male sterility factor that is compensated for by the action of the male fertility restorer gene product contained in the first plant. The cytoplasmic male sterility factor of the present invention is novel, although it may be related to or variants of any of the aforementioned C, S, or T cytoplasmic male sterility factors. The cytoplasmic male sterility factor of the present invention is selected as further described hereinbelow. Such a method may be used with any suitable species, preferably a species that reproduces by sexual means, such as maize, sorghum, and any of the various other plants aforementioned herein with respect to other embodiments of the present invention.

The second plant is genetically divergent from the first plant having the nucleic acid of the present invention, and exhibits cytoplasmic male sterility (CMS) because it carries a CMS factor, i.e., a gene or genes that confers CMS on a plant. When these two plants, or lines or varieties derived therefrom, are co-cultivated and allowed to cross-pollinate, the pollen of the first plant of the present invention cross-pollinates the second plant, resulting in fertile hybrid seeds. The hybrid seeds are fertile because the CMS factor of the second plant is compensated for by the action of the nuclear restorer gene active in the first plant. This method of producing a hybrid seed is identical to that described in the Background section of this specification with respect to C, S, or T cytoplasms that confer or contain CMS factors resulting in cytoplasmic male sterility that is reversible by suitable nuclear restorer genes. The invention provided hereby is novel in that novel CMS factors may be identified and incorporated into this known method of hybrid seed production in accordance with conventional breeding techniques. Such new CMS factors are discussed further hereinbelow.

The nucleic acids of the present invention may be used in another method, which generates new CMS variants or factors comprising the steps of: (a) constructing a nucleic acid comprising a nucleotide sequence that encodes a male fertility restorer gene product; (b) inserting the nucleic acid into plant cells; (c) culturing the cells, thereby generating a first plant; and (d) selecting a second plant that is cytoplasmic male sterile, which when crossed by the first plant produces fertile seed.

Such new CMS variants may be generated using any suitable cloned nuclear restorer (rf) polynucleotide sequence. For purposes of setting forth the general method, rf2 will be used as an example; the method, of course, is not limited only to rf2, however. Accordingly, recombinant (i.e., containing the cloned polynucleotide that specifies the nuclear restorer gene, or portions thereof) plants can be used in the following fashion: Using methods generally known in the art, a line homozygous for leaky mutant alleles of rf2 (or another housekeeping gene product present in the mitochondria, the chloroplast or cytosol) via backcrossing, mutagenesis, or homologous recombination can be generated. The leaky mutant alleles may, for example, represent minor amino acid substitutions that only slightly impair the function of the housekeeping gene product. Alternatively, the leaky mutants might arise via altered regulatory sequences, such that the gene product is present at somewhat less than optimal amounts. Such alleles should condition male fertility in normal cytoplasms but cause or allow male sterility in certain novel cytoplasms. The leaky alleles of rf2 (or other housekeeping genes) could be identified as naturally occurring variants, selected from mutagenesis experiments or created via genetic engineering. Polynucleotide sequences of such leaky alleles include SEQ ID NO:1, and sequences that hybridize thereto under moderate or more stringent conditions, as described hereinabove. Novel cytoplasms of a second plant that result in fertile $F_1$ seed upon crossing by the first plants having one of the aforementioned leaky alleles would contain one or more genetic defects such that they conditioned male fertility in a completely wild-type nuclear genome, but male sterility when associated with a nuclear genome that contained a leaky housekeeping gene. Such novel cytoplasms could be identified as naturally occurring variants, selected from mutagenesis experiments or created via genetic engineering. Because plants carrying the novel cytoplasm and homozygous for the leaky mutation of the housekeeping gene would be male sterile, they would be useful for the production of hybrid seed, as set forth hereinabove. The resulting hybrid seed would be male fertile if the male parent of the hybrid carried a wild-type allele of the housekeeping gene. In particular, considering the possible detoxifying function of the rf2 gene product, the same procedures may be followed wherein the housekeeping gene function is to restore the activity of a second gene product's activity by, for example, removing aldehyde groups that are destabilizing or otherwise improving the functioning of the second gene product.

The nucleic acid that is used in the inventive methods hybridize under at least moderately stringent hybridization conditions to a DNA that includes nucleotide sequences specific to a gene selected from the group of maize rf genes, as disclosed above. Such DNA preferably is flanked with a regulatory DNA sequence, such that a new plant variety, or cells thereof, derived from the aforementioned procedure, expresses its extra or altered rf genes in a developmentally and/or tissue-specific fashion.

The method of the present invention is used to establish a new CMS plant variety of any suitable plant. Preferably, such a plant reproduces sexually, such as maize, soybean, rapeseed, canola, cotton, safflower, peanut, palm, beet, sorghum, and sunflower. More preferably, the method is used to produce new varieties of maize and sorghum; and most preferably, the method is used to produce new varieties of maize.

The present invention also relates to any suitable organism comprising the vector comprising a nucleic acid comprising a nucleotide sequence that encodes a nuclear restorer gene product of a plant. A suitable organism can be any suitable plant, yeast, or bacteria, such as discussed hereinabove regarding suitable plants from which to isolate the restorer genes and regarding suitable hosts in which to insert the enriched or isolated nucleic acid of the present invention. Preferred organisms are sexually-reproducing plants, as described above. A seed-bearing plant that hosts a vector/nucleic acid construct can bear seeds that themselves include the construct, which seeds also constitute a preferred embodiment of the present invention.

Finally, a plant cell hosting a vector/nucleic acid construct of the present invention constitute another preferred embodiment. Such cells can be cultured and kept as plant tissue culture cells, or certain plant hormones known in the art may be included in the culture media, thereby causing the plant tissue culture cells to differentiate and thereby form a new plant variety. Such plant culturing methods useful in the performance of this aspect of the invention are well known in the art. Such a new plant variety may be fertile or unfertile.

The following examples further illustrate the present invention, but, of course, should not be construed as in any way limiting its scope.

EXAMPLE 1

This example illustrates the use of two different transposon systems in maize for the selection of lines of plants that carry male fertility nuclear restorer genes.

For tracking the mutagenesized chromosomes derived from crossing a transposon-carrying line to a genetically-marked non-transposon line, the following markers, arranged on the following restriction fragment length polymorphism (RFLP) maps of maize chromosomes 3 and 9, among others, were used. These maps are based on Wise et al., *Theor. Appl. Genet.*, 88, 785–795 (1994), in which rf1 and rf2 were mapped to positions on chromosomes 3 and 9, respectively, with reference to closely-linked RFLP markers using five populations of maize. Analysis of RFLP markers was accomplished using conventional methods of DNA analysis (see Sambrook et al., supra).

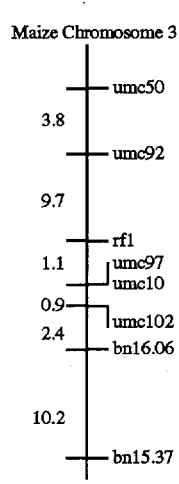
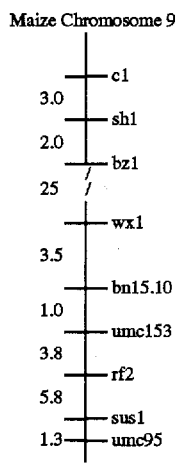

Crosses used to place the location of the rf1 and rf2 genes include those recited in the following table, as further described in Wise et al., id. The sources of genetic stocks used for the crosses described herein are disclosed in Wise et al., id.

stocks carrying certain transposon systems, i.e., Mutator, Cy, or Spm, were used to tag the genes of interest. Gene tagging using naturally-occurring transposons such as those just listed is described by Walbot, *Ann. Rev. Plant Physiol. Plant Mol. Biol.*, 43, 49–82 (1992). This method was used to identify previously mapped rf genes. Specifically, rf1 and rf2 were targeted in the following isolation plot cross using the method of Peterson, in *Maize Breeding and Genetics* (D. B. Walden, ed., John Wiley & Sons, New York, N.Y., 1978), pages 601–631 (the female parent is listed first in all crosses herein):

Cross 1: T Rf1/Rf1 rf2 wc1/rf2 wc1 (inbred R213)×N rf1/rf1 Rf2 wc1/Rf2 wc1 Mutator Cross 2: T Rf1/Rf1 rf2 wc1/rf2 wc1 (inbred R213)×N rf1/rf1 Rf2 wc1/Rf2 wc1 Cy Cross 3: T Rf1/Rf1 c Sh Bz1 Wx1 rf2/c Sh Bz1 Wx1 rf2 (inbred R213)×N rf1/rf1 c1-m5 Sh Bz1 wx1-m8 Rf2/c Sh Bz1 wx1 Rf2

In the absence of mutation, progeny kernels from each cross are heterozygous for the wild-type Rf allele and should therefore yield wildtype seedlings. Only if a gamete from the transposon-containing parent carries a newly generated mutant allele (e.g., via the insertion of a Mu1 element, signified as rf2-m, for example).

The results of these crosses, including origin, size, and mutation rates in transposon populations screened for male-sterile mutations in maize, are presented below:

| | | Maize populations used for mapping rf1 and rf2 with RFLP and visible markers. | | | |
|---|---|---|---|---|---|
| Population | Cross type | No. of progeny | Parent 1 | Parent 2 | Traits scored |
| Rf1 | | | | | |
| 92 1267–68* G16 | BC$_1$ | 96 | R213-T1g16 [Rf1rf1, rf2Rf2]⁺ | g16-N [rf1rf1,Rf2Rf2] | Rf1-mediated male fertility |
| 92 1140–43 92 2117–118 RG1 | F$_2$ | 102▲ | Q66-N [G16G16] | g16-N [g16g16] | g16 |
| 92g 5029–63 | TC | 89 (6 selected)● | R213-T/Acc731 [Rf1rf1 rgRg rf2Rf2] | g16-N [rf1rf1 rgrg Rf2Rf2] | Rf1-mediated male fertility Rg1 |
| RF2A | | | | | |
| 91g 6222–30 | BC$_1$ | 41 | R213-T [Rf1Rf1,rf2rf2] | rf2-m 8904/R213-N [rf1rf1,rf2Rf2] | Rf2-mediated male fertility |
| RF2B | | | | | |
| 92 1101–05 | BC$_1$ | 903 (86 evaluated for RFLP markers) | R213-T/wx-m8 [rf1Rf1,Rf2rf2] | R213-N [Rf1Rf1,rf2rf2] | Rf1- and Rf2-mediated male fertility |

*Pedigree numbers associated with this population
⁺Parental genotype. See Wise et al, supra.
▲Selected for homozygous g16.
●Ragged, male-fertile plants carrying a recombination between the rg and rf1 loci were selected.

Based on the knowledge gained from the indicated classical genetic crossing studies, using the RFLP markers,

| Population | Subpopulation | Transposon donor source* | No. of rf2-m alleles isolated | Population size | Mutation rate no./100,000 gametes |
|---|---|---|---|---|---|
| Mutator | YA | Mu⁴ outcross (1220) | 1 | 8,500 | |
| | P | Mu² outcross (1120) | 1 | 12,000 | |
| | G | Mu¹ outcrosses (1212, 1215, 1218, 1219) | 3 | 5,000 | |
| | OB | Mu² outcross (1118) | 0 | 12,000 | |
| | B | Mu² outcross (1121, 4938) | 0 | 9,700 | |
| | m | Mu outcrosses (1207, 1216, 1222, 1224) | 0 | 3,100 | |
| Mutator population total | | | 5 | 50,300 | 9.9 |
| Cy | OA/BB | 1230–1234, 3919–3921 | 1 | 28,000 | |
| Cy population total | | | 1 | 28,000 | 3.6 |

-continued

| Population | Subpopulation | Transposon donor source* | No. of rf2-m alleles isolated | Population size | Mutation rate no./100,000 gametes |
|---|---|---|---|---|---|
| Spm | CV | Revertants from c1–m5 | 0 | 20,000 | |
| | c1–m5 | "Control" | 1 | 80,000 | |
| Spm population total | | | 1 | 100,000 | 1.0 |

*Transposon donor sources are indicated by the pedigree numbers. Mu outcross, Mu$^2$ outcross, and Mu$^4$ outcross are defined by Robertson, Mol. Gen. Genet., 191, 86–90 (1983).

The seven heritable rf2-m alleles so derived from the aforementioned Mutator and Spm transposon stocks and their progenitor allele were as follows:

| Allele | Progenitor Allele |
|---|---|
| 8110 | Q66 |
| 8122 | Q67 |
| 9323 | Q67 |
| 9385 | n.d. |
| 9390 | Q66 |
| 9437 | Q67 |
| 8904 | n.d. |

Accordingly, transposon-generated mutants at the rf2 genetic locus were isolated and thus available for experiments directed to isolating the rf2 gene and/or cDNA.

EXAMPLE 2

This example illustrates a method for isolating the rf2 gene from the rf2-m lines described in Example 1.

A Mu1 transposon was shown to cosegregate with one of the alleles identified in Example 1 and Schnable et al., Genetics, 136, 1171–1185 (1994), i.e., rf2-m8122. As shown in FIG. 1A, cosegregation analysis was performed on a representative subset of 56 male-sterile (rf2-m8122/rf2-ref) and 49 male-fertile siblings (Rf2/rf2-m) from two segregating families derived from the cross: T cytoplasm Rf1/Rf1 rf2-R213/rf2-R213×Rf1/Rf1 Rf2/rf2-m8122. A 3.4 kilobase, Mu1-hybridizing EcoRI/HindIII restriction fragment is present in male-sterile siblings, but absent in male-fertile siblings in both of these segregating families. This DNA fragment was cloned into PF#9, which is an E. coli strain transformed by the plasmid pRf2 (see FIG. 2), as further discussed hereinbelow. Lanes are indicated as follows: OE, DNA isolated from the original male-sterile plant in which the rf2-m8122 allele was first identified. This plant had the genotype rf2-m8122/rf2-R213. GPP, GP, and P refer to the great-grandparent, grandparent and parent, respectively, of one of the segregating families. Each of these ancestors had the genotype rf2-m8122/Rf2. S and F refer, respectively, to male-sterile and male-fertile siblings within the segregating family.

Figure 2:
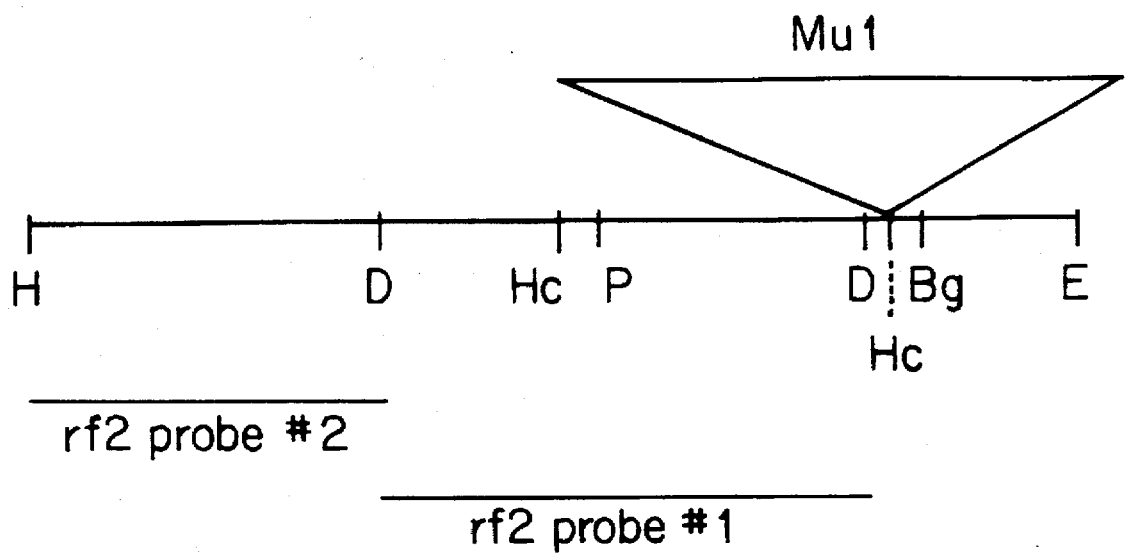
FIG. 2 is a restriction endonuclease map of pRf2.

Using standard recombinant DNA techniques, total DNA from a single male-sterile plant that carried rf2-m8122 was subjected to preparative EcoRI/HindIII digestion and size-selected DNA was isolated for ligation into the lambda phage vector NM 1149 (Murray, The Bacteriophage Lambda, Hendrix ed. (1983)). The 3.4 kilobase EcoRI/ HindIII fragment released from a Mu1-positive lambda phage (named λ91 8122 #9) isolated from the resulting library was subcloned into plasmid vectors pBSK or pBKA (Stratagene), and named prf2. The prf2 plasmid was used to transform E. coli DH5α or XL1-Blue MRF', which transformed strain is referred to as PF#9. A restriction site map of the insert of the prf2 plasmid is shown in FIG. 2, wherein H stands for HindIII, D stands for DraI, Hc stands for HincII, P stands for PstI, Bg stands for BglII, and E stands for EcoRI. The location of the Mu1 insertion point is clearly marked therein between the second DraI and BglII restriction sites.

Figure 1B:
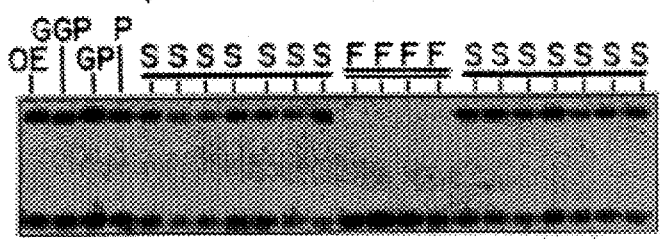

FIG. 1B is the autoradiographic representation of the DNA blot of FIG. 1A after removing the Mu1 probe and reprobing the blot with pRf2 fragment #1 (see FIG. 2). The result as depicted establishes that the cloned DNA is derived from the 3.4 kb Mu1-hybridizing EcoRI-HindIII fragment present in sterile but not fertile siblings.

EXAMPLE 3

This example illustrates methods for verifying the identity of the rf2 clone described in Example 2, and results thereof.

The identity of the rf2 genomic clone described above was confirmed via allelic cross-referencing experiments, as follows: A single-copy fragment from pRf2 (i.e., rf2 probe #1, FIG. 2) was hybridized to DNA derived from five independent rf2 mutants and their respective wild-type progenitor alleles, which are recited in Example 1. The results, revealed polymorphisms between each rf2-m allele and its corresponding wild-type progenitor allele. Specifically the rf2m-8122 allele is associated with a slower moving restriction fragment (i.e., a fragment with lower gel electrophoretic mobility). than is the progenitor Q67 allele. Similarly, rf2m-8110 differs from its progenitor Q66, rfm-9323 differs from its progenitor Q67, and rf2m-9390 differs from its progenitor Q66.

Accordingly, the pRf2 includes at least a portion of the sequence of the rf2 gene.

EXAMPLE 4

This example illustrates the nucleotide sequence of the rf2 insert of a cDNA clone identified using the insert of the pRf2 plasmid, as discussed in Example 2. Additionally, this example illustrates the results from comparing the rf2 cDNA nucleotide sequence to those sequences stored in publicly available gene databases.

Using $^{32}$P radiolabeled rf2 probes #1 and #2 (shown in FIG. 2) in combination, a cDNA library derived from mRNA isolated from immature maize tassels and cloned into λGT10 phage was screened, in accordance with methods well-known in the art (see Sambrook et al., supra; the cDNA library, named ts2, was a gift of S. Delaporta of Yale University). From a first screen, six putative positive plaques of phage were identified, which, upon a series of two rescreenings, were resolved to include three verified positive plaques. DNA from the positive phage were analyzed as to its ability to hybridize back to the aformentioned probes #1 and #2, and size of insert. The phage having the largest included insert was selected for subcloning that insert into plasmid pBSK and pBKA (Stratagene) for sequencing studies. The cDNA clone used for sequencing was named rf2 cDNA 6-2-8-1.

As determined by conventional methods of nucleic acid sequencing (Sambrook et al., supra), the partial sequence of the insert of the rf2 cDNA clone 6-2-8-1, from the 5' end, is:

| | | | | |
|---|---|---|---|---|
| 1 CTTTTCCTCT | TCTGATGTAT | GCCTGGAAAG | TTGGCCCTGC | TTTGGCATGT |
| 51 GGAAATACTC | TCGTGCTCAA | GACTGCTGAA | CAAACCCCTC | TATCGGNTTT |
| 101 GTATATCTCC | AAATTGTTGC | ATGAGGCTGG | ACTACCTGAG | GGTGTTGTGA |
| 151 ATGTCGTTTC | TGGTTTTGGN | CCTACTGCTG | GTGCTGCTCT | TGCTAGTCAC |
| 201 ATGGATGTTG | ATAAGATCGC | ATTTACTGGA | TCTACCGATA | CTGGAAAAAT |
| 251 TATTCTCGAG | TTGGCTGCAA | AGAGCAACCT | TAAGACAGTG | ACACTGGAGT |
| 301 TAGGAGGAAA | GTCCCCTTTC | ATCATATGGA | CGAAGCTGAT | GTTTGGACCA |
| 351 GCTNTTGGAG | CTTGNGCANC | TTGGCCTGTN | CTTTTACCAG | GANAATGCTG |
| 401 TA | | | | |

[SEQ ID NO: 1]

Using the National Center for Biotechnology Information (NCBI) Experimental GENINFO(R) BLAST Network Service (Blaster), SEQ ID NO:1 and a translated corresponding amino acid sequence of SEQ ID NO:1 (i.e., SEQ ID NO:2) were compared to the amino acid sequences included in at least the following databases: (1) Brookhaven Protein Data Bank, April 1994 Release; (2) SWISS-PROT, Release 30.0, October 1994, Release 41.10 (complete), Sep. 19, 1994; (3) GenBank(R), Release 85.0, Oct. 15, 1994; (4) Kabat Sequences of Proteins of Immunological Interest Release 5.0, August 1992; (5) TFD Transcription Factor (protein) Database, Release 7.0, June 1993; (6) Ancient Conserved Region subset of SWISS-PROT, Dec. 3, 1993; (7) Translations of select Alu repeats from REPBASE NUCLEOTIDE SEQUENCE DATABASES; (8) EMBL Data Library, Release 40.0, September 1994; (9) Vector subset of GenBank(R) 82.0, Apr. 11, 1994; (10) Kabat Sequences of Nucleic Acid of Immunological Interest, Release 5.0, August 1992; (11) Eukaryotic Promoter Database, Release 35, June 1993; (12) Database of Expressed Sequence Tags (cumulative daily update); and (13) Database of Sequence Tagged Sites, Release 1.5, Oct. 26, 1994.

The sequence of SEQ ID NO:1 and its correspondent amino acid sequence [SEQ ID NO:2] were compared to the contents of the above-stated databases. In all, greater than 132,000 sequences are contained in those databases. The result from the computer database search is that the rf2 gene is highly related to aldehyde dehydrogenase from a variety of species, including Bos taurus (73% homology), Ovis aries (73% homology), horse (74% homology), *Aspergillus niger* (86% homology), and *homo sapiens* (86% homology). In particular, SEQ ID NO:1 shares substantial homology with both mitochondrial and cystolic aldehyde dehydrogenase from human, rat, *Aspergillus n.* and other species.

This example provides the strong suggestion that rf2 encodes a common enzymatic function, aldehyde dehydrogenase, which can be viewed as a necessary mitochondrial activity, and/or which can be viewed as a necessary detoxifying activity to restore a vital mitochondrial activity.

EXAMPLE 5

This example illustrates the use of the cloned rf2 genes for the generation of new cytoplasmic male sterility systems.

The present invention may be used to generate multiple CMS systems that could be mixed in the same way as the C, S and T systems are now, thereby providing a greater variety of genetic backgrounds for hybrid seed production. Because rf2 looks like a basic housekeeping gene, i.e., aldehyde dehydrogenase, leaky mutations (such as that presumably carried by the rf2-ref allele) do not give a phenotype in normal cytoplasms. For example, rf2/rf2 plants having an N cytoplasm are male fertile. However, in a different cytoplasm (such as T) that is already weakened (such as T), the synergistic effects of the rf2 mutation and the cytoplasmic mutation effectively lead to male sterility.

Accordingly, for the identification of new CMS systems, one combines mutated cytoplasms or existing variants of N that are "weakened" and mutated genes like rf2 that are associated with the mitochondria or cytosol. In combination, these two mutants serve as a CMS/restorer system. One can use such an approach in any species, and one could make as many CMS systems as desired. This invention has broad cross-species applicability in view of the close homology of SEQ ID NO:1 between proteins found in such evolutionarily distant organisms as maize and cows.

In addition, "strong" mutants (e.g., complete loss of function) of rf2 may display a male sterile phenotype in normal cytoplasms. As such these alleles could be used in the Pioneer system, for example, described above.

Strong alleles associated with a lack of function include the transposon-induced alleles described in Schnable et al., *Genetics*, 136, 1171–1185 (1994). The phenotype of such alleles would be consistent with having no gene product associated therewith, such that a northern blot experiment would support the proposition that these alleles do not produce a transcript. Transferring the mutant alleles to an N cytoplasm and allowing such plant to self-pollinate would then provide rf2/rf2 genotypes in an N cytoplasm, which will be male sterile.

Accordingly, the rf genes identified herein have utility in the production of new CMS systems, which will benefit hybrid seed production and allow for a broader gene pool in the general cultivated plant community.

EXAMPLE 6

This example illustrates the cloning of the rf1 gene.

The same strategy was used for the isolation of rf1 clones as was used for the isolation of rf2 clones, that being to use transposon lines to introduce tags that can be found with available transposon probes. As mentioned above, following a directed transposon tagging experiment, it is necessary to use linked markers (as identified in the map of Maize Chromosome 3 above) to distinguish between the newly induced mutants and the recessive allele used to uncover them. To identify an rf1 donor line with distinctive RFLP alleles flanking rf1, chromosome 3 RFLP fingerprints of five rf1 inbreds (W22, B37, Mo17, W64A, and B73) were obtained. These inbreds were RFLP finger printed by digesting their respective DNAs with 8 restriction endonucleases (BamHI, EcoRI, EcoRV, HindIII, KpnI, DraI, BclI, and BglII), followed by Southern blotting with RFLP markers that flank rf1. The results from this survey established that rf1-B37 can easily be distinguished from the Rf1-Ky21 or Rf1-WF9 alleles present in the Mutator population by using the restriction enzyme, DraI, in conjunction with umc10 and umc92, which flank rf1 (see above).

Using the aforestated strategy and tools, Mutator-induced male-sterile mutants of the rf1 fertility-restorer locus have been identified. The Rf1 Rf2 Mutator lines were crossed by the inbred line B37, which has the genotype rf1/rf1,Rf2/Rf2, thereby providing Cross 4:

T Rf1/Rf1 (Mutator) ×N rf1-B37/rf1-B37.

The parents used in Cross 4 and all subsequent crosses are plants that are homozygous for Rf2. In this cross, as in the previously recited crosses, T and N refer to T and N cytoplasms, respectively.

In the absence of mutation, the progeny from cross 4 are male-fertile because, although they have T cytoplasm, they carry at least one copy of each of the two dominant nuclear restorer factors, Rf1 and Rf2. However, if the Rf1 locus was inactivated by a Mu element insertion in a given progeny, then that plant would be male sterile. These exceptional plants putatively carry Mutator-induced rf1 alleles. Progeny of Cross 4 ($\bar{=}$123,500) have been screened for mutations at rf1; ten putative male-sterile mutants have been identified.

To confirm the heritability of the putative male-sterile mutants and determine if the male-sterile phenotype is associated with the rf1 locus, the following experiments were performed on three of the putative male-sterile mutants: Exceptional male-sterile plants from Cross 4 (with the predicted genotype: T cytoplasm, rf1-Mu/rf1-B37, Rf2/Rf2) were crossed as shown in Cross 5: T rf1-Mu rg+/rf1-B37 rg+X T Rf1 Rg/rf1 rg+, wherein rg+refers to the normal wild type allele found in most maize lines.

Plants with the genotype rf1-Mu rg+/Rf1 Rg were predicted to constitute 25% of the progeny from Cross 5 and can be identified based on their ragged phenotype and previously characterized DNA polymorphisms at chromosome 3 of each of WF9, Ky21, B37 and our Rf1 Rg stock. Based on their pedigree, rf1-Mu alleles should be in coupling with Ky21- and/or WF9-derived RFLP markers which are easily distinguished from those flanking rf1-B37. Plants derived from Cross 5 and having this target genotype were crossed as males on a T-cytoplasm W64A (rf1/rf1 Rf2/Rf2, see cross 6) as follows:

Cross 6: T rf1/rf1 (W64A)×T rf1-Mu rg+/Rf1 Rg Heritable male-sterile mutations from Cross 6 are expected to segregate 1:1 (male sterile:male fertile), whereas, rows derived from non-heritable male-sterile "mutants" will consist entirely of male-fertile plants. If the male-sterile mutation is at the rf1 locus, male-sterile and male-fertile plants will be normal and ragged, respectively (except for rare crossovers). Based on these tests, of the three mutants tested, two were shown to represent rf1-Mu alleles.

As noted above in Example 2, Mutator-tagged alleles can be cloned using a sequence homologous to the inserted Mu transposon as a molecular probe. However, Mu elements are present in multiple copies in the genomes of Mutator-derived stocks (see Bennetzen, *Proc. Natl. Acad. Sci. USA*, 81, 4125–4128 (1986)). Therefore, the first step in cloning a gene tagged with a Mu element is to identify the individual Mu element inserted at the mutant locus.

Co-segregation analysis with Mutator-specific hybridization probes may be performed for the purpose of identifying the individual Mu element inserted at an rf1-Mu allele: Because these rf1-Mu alleles have been isolated from Mutator populations (Cross 4), they may be associated with Mu element insertions. DNA flanking such Mu elements would have a high probability of representing rf1 sequences. Co-segregation analyses were used to identify the specific Mu elements responsible for a given mutation. The families resulting from Cross 6 and carrying rf1-Mu3207 and rf1-Mu3310 segregated 1:1 for male-sterile normal (rf1-Mu rg+/rf1-B37 rg+) and male-fertile ragged (Rf1Rg/rf1-B37 rg+) plants. DNA from each individual sibling was digested for such tests with HindIII and/or EcoRI). Mu1-specific sequences were used to probe genomic Southerns blotted with these DNAs. For each rf1-Mu allele, a Mu1-containing DNA fragment was identified that cosegregated with the mutant allele in over 40 progeny. These DNA fragments have been cloned using procedures as described in Example 2, and related procedures well-known in the art. DNA flanking a Mu1 element that co-segregated with male sterility in these crosses would have a high probability of representing rf1 sequences. Allelic cross-referencing experiments, as described above in Example 3, will be used to establish whether the cloned sequences indeed represent rf1.

All of the references cited herein, including patents, patent applications, and technical literature, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

---

What we claim is:

1. An enriched or substantially isolated nucleic acid comprising a nucleotide sequence that hybridizes at least under moderate stringency conditions to SEQ ID No:1 or SEQ ID No:3 and is capable or restoring male fertility to a plant having a cytoplasmic male-sterility trait.

2. The nucleic acid of claim 1, wherein said nucleotide sequence that hybridizes to SEQ ID NO:1 or SEQ ID NO:3 and is capable of restoring male fertility to a plant having a cytoplasmic male-sterility trait is Rf2.

3. The nucleic acid of claim 1, wherein said plant is selected from the group consisting of maize, soybean, rapeseed, canola, cotton, safflower, peanut, palm, sorghum, beet, and sunflower.

4. The nucleic acid of claim 3, wherein said plant is maize.

5. The nucleic acid of claim 1, wherein said nucleic acid is SEQ ID NO:1 or a polynucleotide having a sequence complementary thereto.

6. A vector comprising a nucleic acid or claim 1 as an insert.

7. A vector comprising a nucleic acid of claim 2 as an insert.

8. A method for the production of hybrid seed, comprising the steps of:

(a) obtaining a nucleic acid of claim 1;
   (b) inserting said nucleic acid into a plant cell;
   (c) establishing a first plant form said plant cell having and expressing said nucleic acid; and
   (d) cross-pollinating a second plant by said first plant, wherein said second plant has a cytoplasmic male sterility factor that is compensated for by the action of said male fertility restorer gene contained in said first plant.

9. The method of claim 8, wherein said plant is maize or sorghum.

10. An organism comprising the vector of claim 6.

11. The organism of claim 10 wherein said organism is selected from the group consisting of plants, yeasts, and bacteria.

12. A seed comprising the vector of claim 6.

13. A plant cell comprising the vector of claim 6.

14. A plant comprising the vector of claim 6.

15. A method for the production of variant CMS factors, comprising the steps of:

(a) obtaining a nucleic acid of claim 1;
   (b) inserting said nucleic acid into plant cells;
   (c) culturing said cells, thereby generating a first plant; and
   (d) selecting a second plant that is cytoplasmic male sterile, which when crossed by said first plant produces fertile seed.

16. The method of claim 15, wherein said nucleotide sequence is SEQ ID NO:1, a polynucleotide having a sequence complementary thereto, or a polynucleotide having a substantially equivalent sequence with respect to SEQ ID NO:1 or its complement.

* * * * *

UNITED STATES PATENT AND TRADEMARK OFFICE
CERTIFICATE OF CORRECTION

PATENT NO. : 5,684,242
DATED : November 4, 1997
INVENTOR(S) : Schnable et al.

It is certified that errors appear in the above-identified patent and that said Letters Patent is hereby corrected as shown below:

In column 11, lines 54 and 55, "Replication systems may be derived from ColE1" should not be in italics.

In column 13, line 47, "$^{32}$p" should read --$^{32}$P--.

In column 14, line 14, "222" should read --223--.

In column 20, line 38, "mobility). than" should read --mobility) than--.

Signed and Sealed this

Twenty-fourth Day of February, 1998

Attest:

BRUCE LEHMAN

Attesting Officer

Commissioner of Patents and Trademarks